(12) United States Patent
Kitano

(10) Patent No.: US 10,080,480 B2
(45) Date of Patent: *Sep. 25, 2018

(54) ENDOSCOPE

(71) Applicant: FUJIFILM Corporation, Tokyo (JP)

(72) Inventor: Ryou Kitano, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 311 days.

This patent is subject to a terminal disclaimer.

(21) Appl. No.: 15/052,845

(22) Filed: Feb. 24, 2016

(65) Prior Publication Data

US 2016/0249789 A1 Sep. 1, 2016

(30) Foreign Application Priority Data

Feb. 27, 2015 (JP) ................................ 2015-038787

(51) Int. Cl.
*A62B 1/04* (2006.01)
*A61B 1/00* (2006.01)
*A61B 1/04* (2006.01)
*H04N 5/225* (2006.01)

(52) U.S. Cl.
CPC ...... *A61B 1/00126* (2013.01); *A61B 1/00114* (2013.01); *A61B 1/00117* (2013.01); *A61B 1/00163* (2013.01); *A61B 1/04* (2013.01); *H04N 2005/2255* (2013.01)

(58) Field of Classification Search
None
See application file for complete search history.

(56) References Cited

U.S. PATENT DOCUMENTS

| 8,679,000 B2 | 3/2014 | Kimura | |
|---|---|---|---|
| 8,956,279 B2 | 2/2015 | Kitano | |
| 2012/0197081 A1* | 8/2012 | Kimura | A61B 1/00124 600/110 |
| 2012/0220825 A1 | 8/2012 | Kimura | |
| 2013/0085328 A1 | 4/2013 | Kitano | |

FOREIGN PATENT DOCUMENTS

| JP | 2013-075026 | 4/2013 |
|---|---|---|
| JP | 5192559 | 5/2013 |
| JP | 5436470 | 3/2014 |

* cited by examiner

*Primary Examiner* — Dakshesh D Parikh
(74) *Attorney, Agent, or Firm* — JCIPRNET

(57) ABSTRACT

An endoscope includes: a solid-state imaging device for photoelectrically converting optical images formed via an imaging lens, a circuit board electrically connected to the solid-state imaging device, a signal cable electrically connected to the circuit board, an optical member holding section that holds the imaging lens or a prism, a connection member, one end of which is fastened to the signal cable and other end of which is provided with engaging pawls to be engaged with the optical member holding section, that connects the optical member holding section to the signal cable, and a mounting member that is mounted on at least part of an outer periphery of the optical member holding section, and the mounting member makes contact with the engaging pawls engaged with the optical member holding section to hold at least part of the engaging pawls between the mounting member and the optical member holding section.

4 Claims, 5 Drawing Sheets

ENDOSCOPE

CROSS-REFERENCE TO RELATED APPLICATIONS

This application claims the benefit of Japanese Patent Application JP 2015-038787, filed Feb. 27, 2015, the entire content of which is hereby incorporated by reference, the same as if set forth at length.

FIELD OF THE INVENTION

The present invention relates to an endoscope.

BACKGROUND OF THE INVENTION

An endoscope has an insertion section to be inserted into, for example, a body cavity of a subject to be examined. This insertion section is composed of a tip hard section, a bending section and a flexible section in this order from the tip end. Furthermore, an observation window, an illumination window, a forceps outlet and an air/water supply nozzle are provided on the tip end face of the tip hard section. Moreover, a camera module is mounted at the position corresponding to the observation window and a light guide is mounted at the position corresponding to the illumination window inside the tip hard section. The bending section is configured by continuously connecting a plurality of articulation ring units, whereby the tip hard section can be directed to a desired direction by wire operation. The flexible section has a length of approximately 1 to 2 min order that the tip hard section can reach a desired observation portion of a subject to be examined.

The camera module is composed of an imaging lens unit and an imaging unit. The imaging lens unit is composed of a plurality of lenses accommodated inside the housing thereof. The imaging unit has an image area sensor, such as a CCD (Charge Coupled Device) or a CMOS (Complementary Metal Oxide Semiconductor), for photoelectrically converting optical images formed by the imaging lens unit into imaging signals. The image area sensor is connected to a transmission cable via a circuit board, such as a flexible board or a sub-board. Furthermore, electronic components for driving the image area sensor are mounted on the flexible board or the sub-board. The signals from the imaging unit are transmitted to an image processing device via the flexible board or the sub-board and the transmission cable. The image processing device performs image processing for the signals and then displays, for example, the images of lesions, on a monitor.

The transmission cable for transmitting the signals from the imaging unit to the image processing device is formed of a compound multi-core cable. Since the transmission cable is inserted into the whole length of the insertion section, the transmission cable is pushed and pulled strongly each time the insertion section is looped or bent. When the transmission cable is pulled, the joint section between the transmission cable and the circuit board may be separated or the transmission cable may be disconnected in some cases.

In the endoscope described in JP-A-2013-75026, a cable connector is disposed in a space between the inner peripheral face of the tip hard section and the image area sensor to avoid problems such as the separation and disconnection described above. One end of the cable connector is fastened to the sheath of the transmission cable and the other end thereof is mounted on the mounting cylinder section of a prism holder constituting the tip hard section. Furthermore, an engaging pawl to be engaged with the tip end face of the mounting cylinder section is formed at the other end of the cable connector. Hence, even in the case that the insertion section of the endoscope is bent repeatedly and the transmission cable is pulled, the tension force is transmitted to the prism holder by the cable connector, whereby the tension force is not applied to the circuit board or the like, whereby problems such as the separation of the joint section between the transmission cable and the circuit board and the disconnection of the transmission cable do not occur.

Moreover, the electronic endoscope described in Japanese Patent No. 5436470 is also provided with a connection member for connecting the lens barrel to the signal cable and for covering at least one face of the prism. In the electronic endoscope, the end section of the cable cover of the signal cable is bonded to the inside of one end section of the connection member using an adhesive, and a pair of pawls formed at the other end section of the connection member is engaged with the rib section of the lens barrel. Hence, even if the signal cable is pulled in a direction away from the connection member, problems such as the separation of the joint section between the signal cable and the circuit board and the disconnection of the signal cable do not occur.

What's more, the endoscope described in Japanese Patent No. 5192559 is also provided with a cable mounting frame for connecting the body of the tip end section to the signal cable. In the endoscope, the engaging piece of the cable mounting frame is inserted into the engaging hole of the body of the tip end section, and the cable mounting frame is mounted rockably on the body of the tip end section, whereby the cable mounting frame is fastened to the sheath of the signal cable. Hence, even if a pushing/pulling force and a bending force are applied to the signal cable, these forces are relieved by the rocking of the cable mounting frame, whereby the durability of the endoscope is improved.

SUMMARY OF THE INVENTION

In the endoscopes described in JP-A-2013-75026, Japanese Patent No. 5436470 and Japanese Patent No. 5192559, although one end of the connection member for connecting the member provided on the tip end side to the cable is fastened to the sheath of the cable, the other end thereof is engaged with the above-mentioned member using an engaging section, such as an engaging pawl or an engaging piece. Furthermore, the connection member is formed of a thin plate. Hence, if a force is applied to the connection member in a direction in which the bending strength thereof is low, the engaging section may be disengaged from the above-mentioned member, and the connection member may be disconnected from the above-mentioned member.

The present invention is made in consideration of the above-mentioned circumstances and is intended to provide an endoscope capable of improving the connection strength of a connection member against the tension force applied to a signal cable.

An endoscope of an aspect of the present invention comprises: a solid-state imaging device for photoelectrically converting optical images formed via an imaging lens, a circuit board electrically connected to the solid-state imaging device, a signal cable electrically connected to the circuit board, an optical member holding section for holding the imaging lens or a prism, a connection member, one end of which is fastened to the signal cable and the other end of which is provided with engaging pawls to be engaged with the optical member holding section, for connecting the optical member holding section to the signal cable, and a mounting member to be mounted on at least part of the outer periphery of the optical member holding section, wherein the mounting member makes contact with the engaging pawls engaged with the optical member holding section to hold at least part of the engaging pawls between the mounting member and the optical member holding section.

The present invention can provide an endoscope capable of improving the connection strength of the connection member against the tension force applied to the signal cable.

Figure 1:
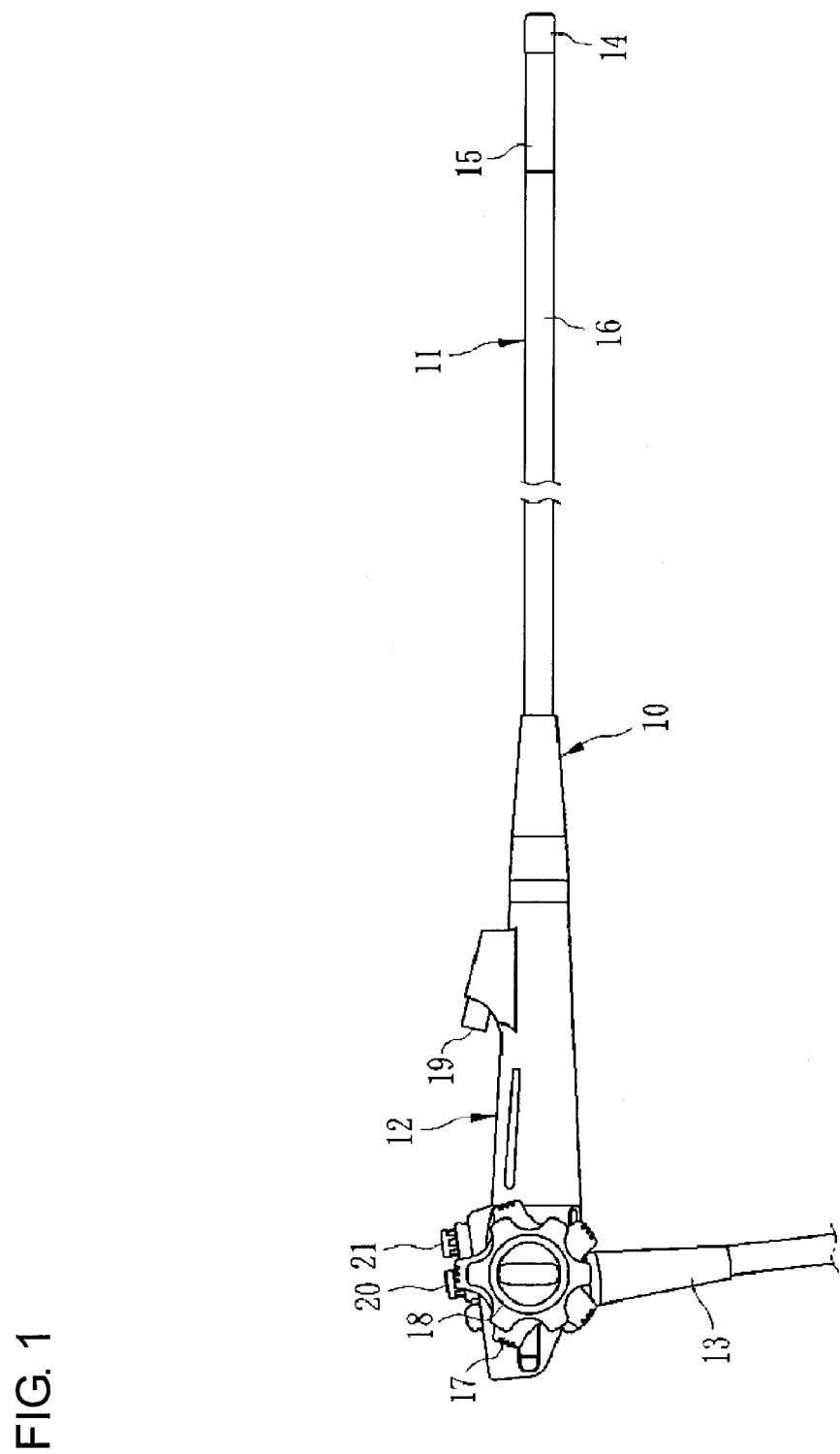
FIG. 1 is an external view showing an endoscope according to an embodiment of the present invention.

DESCRIPTION OF REFERENCE NUMERALS AND SIGNS 1 camera module
10 endoscope
11 insertion section
12 operation section
13 universal cord
14 tip hard section
14a front end section
15 bending section
16 flexible section
17, 18 angle knobs
10 forceps port
20 air/water supply button
21 suction button
22 observation window
23 forceps outlet
24 air/water supply nozzle
25 objective optical system
26 lens barrel
27 prism
28 cover glass
29 image area sensor
30 forceps channel
31 peripheral skin
32 cylindrical section
33 prism holder
33a mounting cylinder section
33b prism mounting frame
34 ring member
34a female screw section
34b engaging pawl
35 flexible board
35g sub-board
36 cover
37 signal cable
38 signal wire
39 cable cover
40 connection member
40a mounting frame section
40b connection plate section
40c arm section
40d pawl section
41 clearance
42 male screw

DETAILED DESCRIPTION OF THE INVENTION

An embodiment of the present invention will be described below referred to FIGS. 1 to 4.

Figure 2:
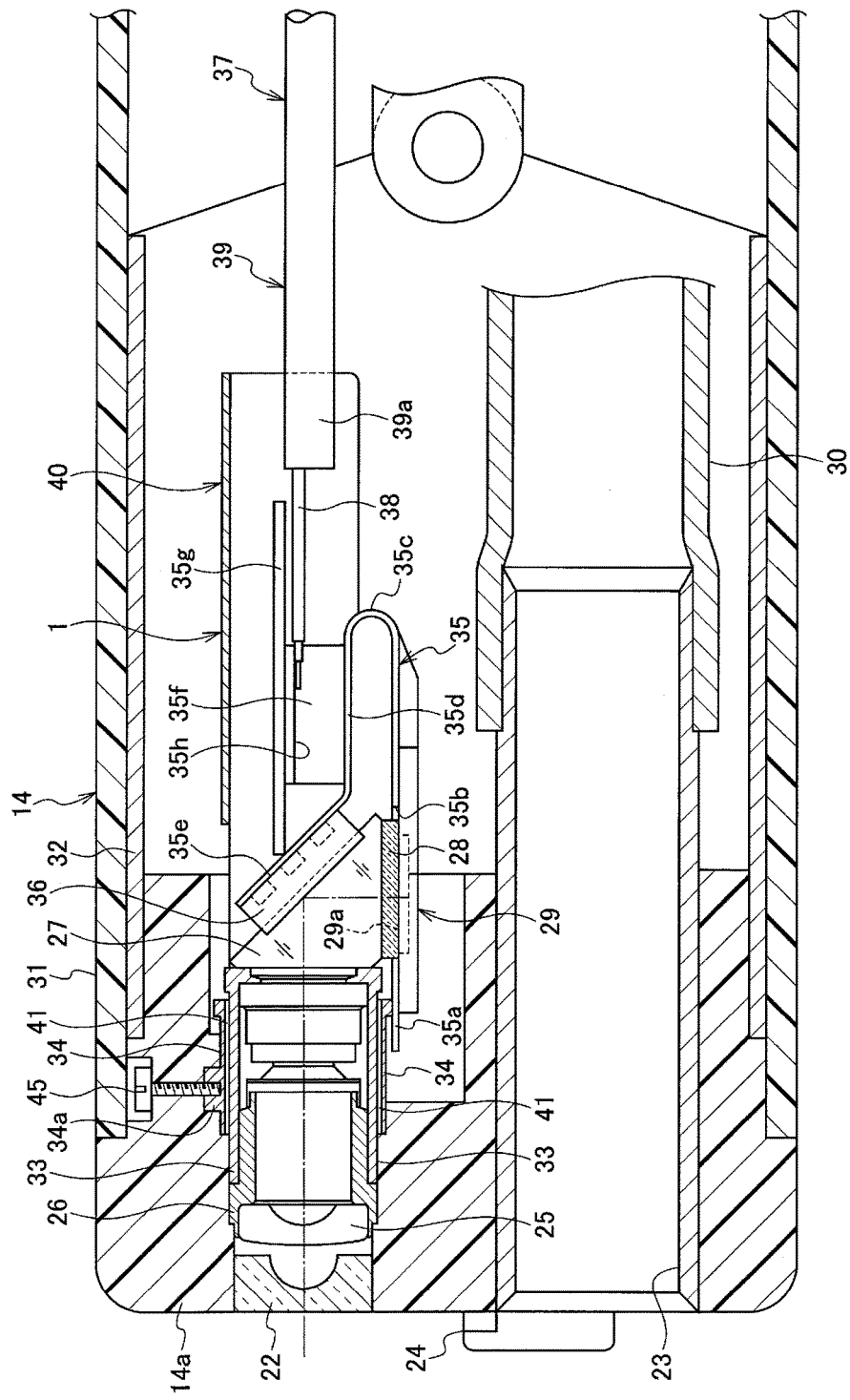
FIG. 2 is a cross-sectional view showing the interior of the tip hard section of the endoscope, viewed from the side and taken on line II-II of FIG. 4.
Figure 3:
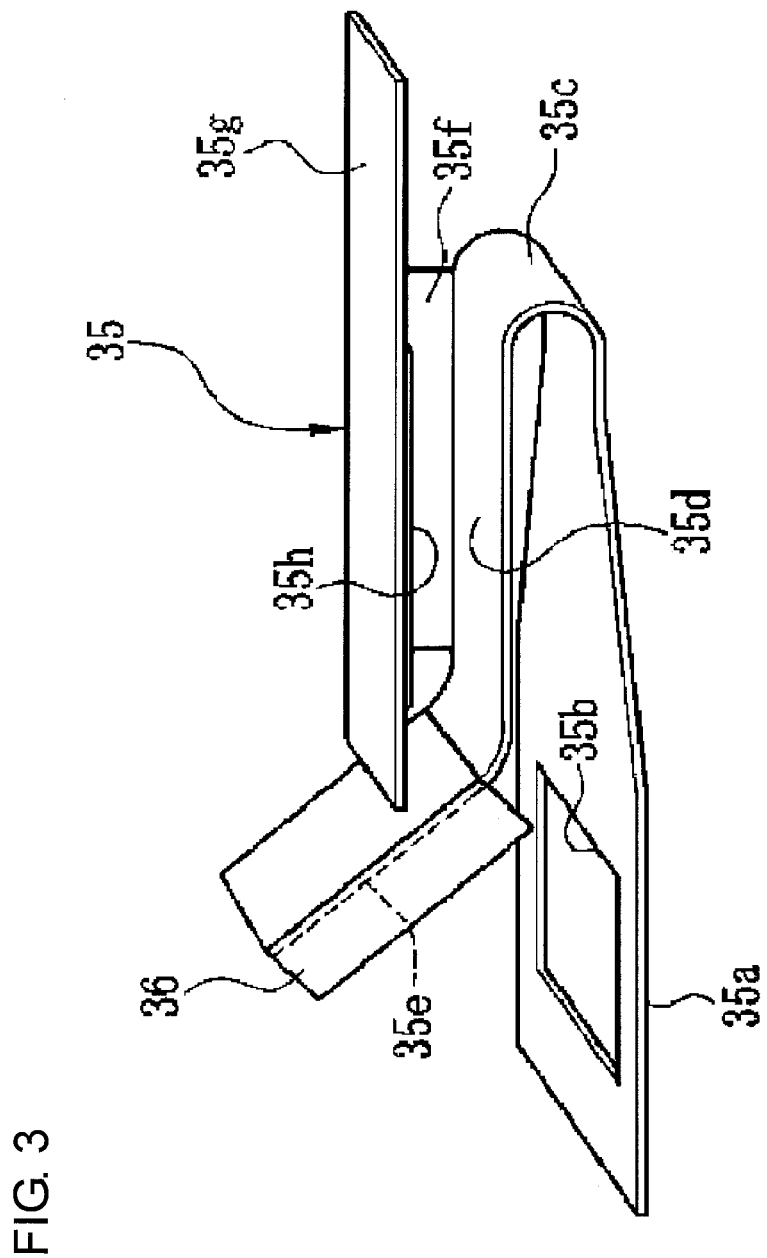
FIG. 3 is a perspective view showing an example of a flexible board.
Figure 4:
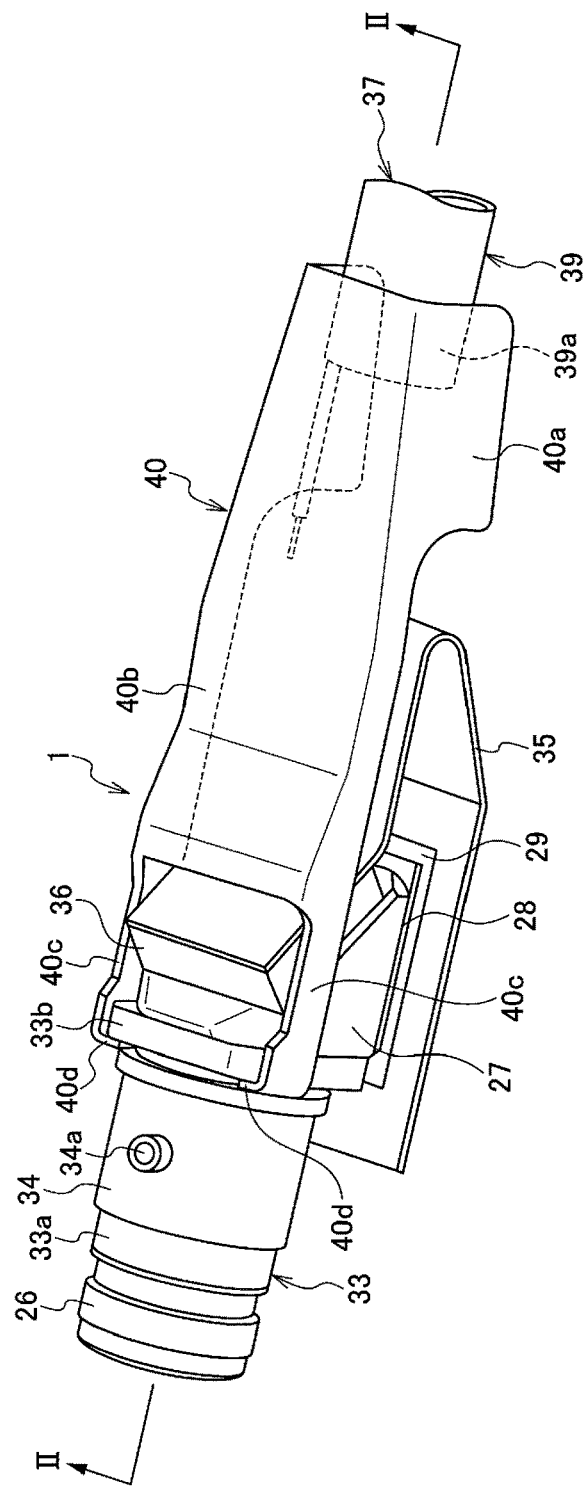
FIG. 4 is a perspective view showing a camera module, viewed from obliquely upward.

FIG. 1 is an external view showing an endoscope according to an embodiment of the present invention. FIG. 2 is a cross-sectional view showing the interior of the tip hard section of the endoscope, viewed from the side and taken on line II-II of FIG. 4. FIG. 3 is a perspective view showing an example of a flexible board. FIG. 4 is a perspective view showing a camera module, viewed from obliquely upward.

As shown in FIG. 1, an endoscope 10 is equipped with a flexible insertion section 11 to be inserted into, for example, a body cavity of a subject to be examined, an operation section 12 provided so as to be connected to the base end portion of the insertion section 11, and a universal cord 13 to be connected to a processor device and a light source device (these two are not shown).

The processor device performs various kinds of image processing for imaging signals input via the universal cord 13 from an image area sensor 29 (see FIG. 2), such as a CCD (Charge Coupled Device) or a CMOS (Complementary Metal Oxide Semiconductor), for photoelectrically converting optical images into imaging signals to convert the imaging signals into video signals and transmits drive control signals for controlling the drive of the image area sensor 29. The video signals converted by the processor device are displayed as endoscopic images on a monitor (not shown) connected to the processor device via a cable.

The insertion section 11 is composed of a tip hard section 14, a bending section 15 and a flexible section 16 in this order from the tip end.

The front end section 14a (the body section of the endoscope 10) of the tip hard section 14 is formed of a hard resin, and the peripheral skin 31 of the tip hard section 14 is formed of a soft resin. A cylindrical section 32 formed of a hard metal material is provided inside the peripheral skin 31 so that one end section thereof is joined to the front end section 14a. As shown in FIG. 2, a camera module 1 to be described later is mounted inside the tip hard section 14.

The bending section 15 is composed of a plurality of articulation rings connected continuously and is bent in the up-down direction and the left-right direction in conjunction with the movement of an angle wire (not shown) inserted into the flexible section 16 by operating angle knobs 17 and 18 provided on the operation section 12. Hence, the tip hard section 14 is directed to a desired direction inside a body cavity, and a portion to be observed inside the body cavity can be imaged using the camera module 1.

The flexible section 16 is a portion having a small diameter and a long length and connecting the operation section 12 to the bending section 15 and has flexibility.

The operation section 12 is provided with a forceps port 19. Treatment tools, such as forceps and injection needles, for use in the treatment of affected parts are inserted into the forceps port 19. The forceps port 19 is connected to a forceps channel 30 (see FIG. 2) disposed inside the insertion section 11, and the forceps channel 30 is connected to a forceps outlet 23 (see FIG. 2) provided in the tip hard section 14.

The operation section 12 is provided with an air/water supply button 20 and a suction button 21. When the air/water supply button 20 is operated, air or a liquid such as water is jetted from an air/water supply nozzle 24 (see FIG. 2) provided on the end face of the tip hard section 14 via an air/water supply channel (not shown) provided inside the insertion section 11. The suction button 21 is operated when objects to be sucked, such as liquids and tissues inside the body, are sucked through the forceps outlet 23.

The configuration of the camera module 1 disposed inside the tip hard section 14 of the endoscope 10 will be described below referred to FIGS. 2 to 5. As shown in FIGS. 2 and 4, the camera module 1 mainly has an objective optical system 25 (imaging lens), a lens barrel 26 (optical member holding section), a prism holder 33 (optical member holding section), a prism 27, an image area sensor 29 (solid-state imaging device), a flexible board 35 (circuit board), a signal cable 37, a connection member 40 and a ring member 34 (mounting member).

As shown in FIG. 2, an observation window 22, an illumination window (not shown), the forceps outlet 23 and the air/water supply nozzle 24 are provided on the end face of the tip hard section 14. The objective optical system 25 for capturing the image light inside a body cavity is disposed inside the lens barrel 26 behind the observation window 22. Furthermore, the prism holder 33 is mounted on the lens barrel 26. The prism holder 33 has a mounting cylinder section 33a that is mounted so as to be fitted on the outer periphery of the rear end side of the lens barrel 26 and a prism mounting frame 33b on which the prism 27 is mounted. The prism mounting frame 33b is provided with an opening through which the image light of an observation portion having passed through the objective optical system 25 is transmitted, and the prism 27 is bonded to the rear end face of the prism mounting frame 33b so as to plug this opening. In other words, the rear end face serves as the end face on which the prism 27 is held by the prism holder 33. The image light of the observation portion having passed through the objective optical system 25 is incident on the prism 27 and is bent inside the prism 27, and an image is formed on the imaging face 29a of the image area sensor 29 via a cover glass 28.

The peripheral section of the image area sensor 29 is made close contact with the outer face of one end section 35a of the slender flexible board 35 so that the imaging face 29a is exposed through the opening 35b (see FIG. 3) formed at the one end section 35a and is electrically connected to the one end section 35a with a bonding wire. The flexible board 35 has a curved section 35c being curved into a U-shape, and the other end section 35e of the flexible board 35 extends to the vicinity of the prism 27 via a straight section 35d extending nearly straight.

A predetermined length of the other end section 35e is bent with respect to the straight section 35d so as to be nearly parallel to the inclined face of the prism 27. A circuit for driving the image area sensor 29 and components (imaginarily indicated by broken lines in FIG. 2) such as an amplifier for amplifying video signals output from the image area sensor 29 are provided on the face of the other end section 35e on the side of the prism 27. A cover 36 is fastened to the other end section 35e, and both the edge sections of this cover 36 are fastened to both the side faces of the prism 27. The above-mentioned amplifier and components are covered and protected with the cover 36. Although the image area sensor 29 and the components, such as the amplifier, generate heat when they are driven, the heat is radiated by the flexible board 35 and the connection member 40 to be described later.

As shown in FIG. 3, in the flexible board 35, a branch section 35f protruding in a direction orthogonal to the longitudinal direction of the straight section 35d and being bent at right angles is provided so as to be connected to the straight section 35d, and a sub-board 35g having a rectangular shape is provided so as to be connected to the tip end section of the branch section 35f. The face of this sub-board 35g is perpendicular to the face of the branch section 35f and is nearly parallel to the face of the straight section 35d. On the inner face of the sub-board 35g, that is, the face on the opposite side thereof, a soldering section 35h is provided, and various signal wires 38 of the signal cable 37 (see FIG. 2) to be described later are respectively soldered to numerous terminals provided on this soldering section 35h.

Returning to FIG. 2, the signal cable 37 is a multi-core cable in which the numerous signal wires 38 are accommodated inside a cylindrical cable cover 39 and is passed through the insertion section 11 and the operation section 12 and inserted into the universal cord 13.

As shown in FIG. 4, the prism mounting frame 33b of the prism holder 33 is connected to the end section 39a of the cable cover 39 by the connection member 40 formed of a nearly T-shaped metal plate. The connection member 40 is composed of a mounting frame section 40a in which both the side sections on one end side of the nearly T-shaped connection member 40 are bent so that the cross section of the connection member 40 is formed into a U-shape, connection plate section 40b formed at the central section of the connection member 40, and a pair of arm sections 40c provided continuously so as to be extended in a slender shape from both the edge sections of the connection plate section 40b toward the other end side of the connection member 40. Pawl sections 40d (engaging pawls) being bent inward toward each other are formed at the respective tip ends of the pair of arm sections 40c, and these pawl sections 40d are engaged with the edges of the prism mounting frame 33b of the prism holder 33. Furthermore, the mounting frame section 40a covers the end section 39a of the cable cover 39, and the clearance between the mounting frame section 40a and the end section 39a of the cable cover 39 is filled with an adhesive, whereby the one end of the connection member 40 is fastened to the cable cover 39 of the signal cable 37. In the state in which the one end of the connection member 40 is fastened to the cable cover 39 and the other end of the connection member 40 is engaged with the prism mounting frame 33b of the prism holder 33, the connection plate section 40b covers the sub-board 35g (see FIGS. 2 and 3).

In this embodiment, the cylindrical ring member 34 fitted on the outer periphery of the rear section of the mounting cylinder section 33a of the prism holder 33 is mounted. The ring member 34 fitted on the mounting cylinder section 33a is disposed so as to be brought close to the prism mounting frame 33b until the rear end of the ring member 34 makes contact with the pawl sections 40d of the connection member 40 engaged with the prism mounting frame 33b of the prism holder 33. Hence, the ring member 34 holds the pawl sections 40d of the connection member 40 between the ring member 34 and the prism mounting frame 33b.

Since the inside diameter of the ring member 34 is slightly larger than the outside diameter of the mounting cylinder section 33a, a clearance 41 is formed between the ring member 34 and the mounting cylinder section 33a. The clearance 41 may be a space serving as an air layer or may be an adhesive layer to be filled with an adhesive that is used to bond the ring member 34 to the prism holder 33. In the case that the clearance 41 is an adhesive layer, the ring member 34 and the prism holder 33 can be integrated with each other.

A female screw section 34a for screw-fastening the ring member 34 mounted on the outer periphery of the mounting cylinder section 33a of the prism holder 33 to a predetermined position inside the front end section 14a of the tip hard section 14 is provided in at least one portion of the outer peripheral section of the ring member 34. As shown in FIG. 2, a male screw 45 is screw-engaged with the female screw section 34a of the ring member 34, whereby the camera module 1 including the ring member 34 is fastened to the interior of the tip hard section 14. The cylindrical section 32 is then fastened to the rear section of the front end section 14a, and the cylindrical section 32 is covered with the peripheral skin 31.

The ring member 34 is not limited to be configured so as to entirely enclose the mounting cylinder section 33a of the prism holder 33 in the circumferential direction but may be configured in a C-shape in cross section so as to enclose at least part of the mounting cylinder section 33a in the circumferential direction. Even in this case, the ring member 34 holds the pawl sections 40d of the connection member 40 engaged with the prism mounting frame 33b of the prism holder 33 between the ring member 34 and the prism mounting frame 33b. Moreover, in the case that the pawl sections 40d of the connection member 40 are configured so as to be engaged with the lens barrel 26, the ring member 34 holds the pawl sections 40d between the ring member 34 and the lens barrel 26.

Figure 5:
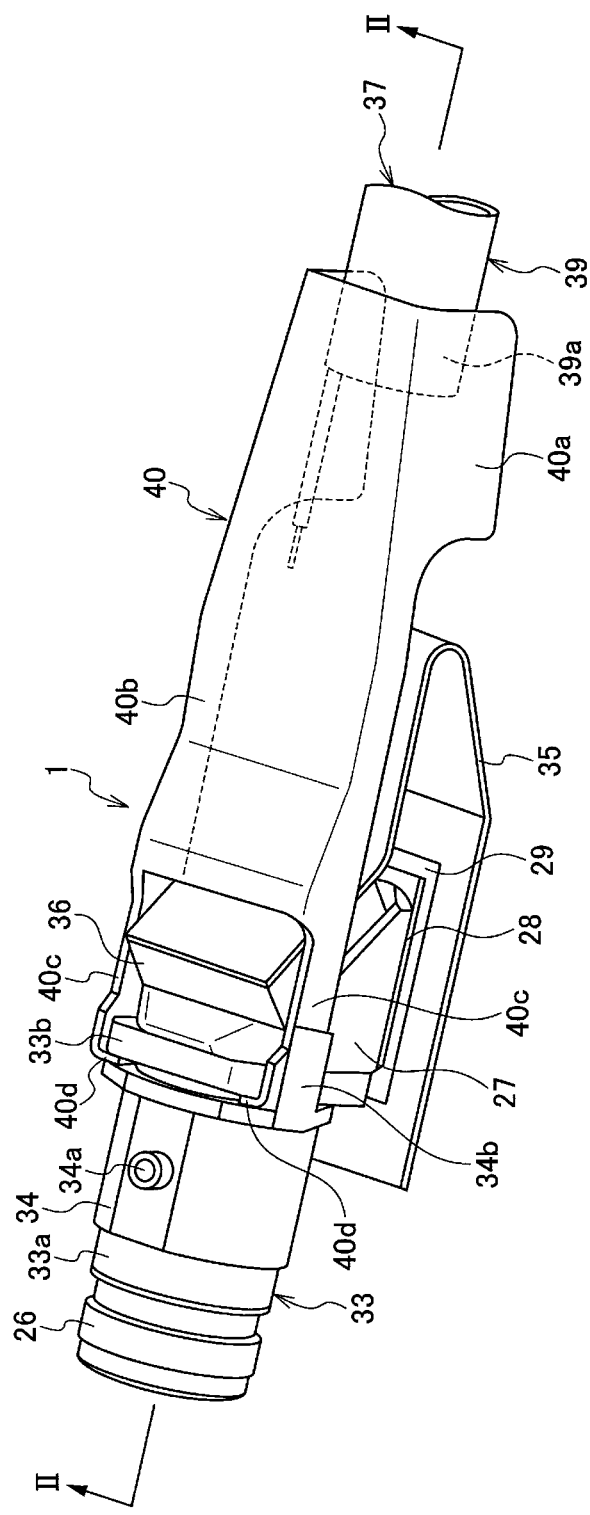
FIG. 5 is a perspective view showing another camera module, viewed from obliquely upward.

What's more, as shown in FIG. 5, the ring member 34 may have a pair of engaging pawls 34b provided continuously so as to be extended in a slender shape from the vicinity of the engaged portion between the ring member 34 and the pawl sections 40d of the connection member 40 toward the rear end side. The engaging pawls 34b stride the rear end face of the prism mounting frame 33b to which the prism 27 is bonded and are engaged with the arm sections 40c of the connection member 40 from the outside. The engaging pawls 34b of the ring member 34 are fastened to the arm sections 40c of the connection member 40 using an adhesive. The fastening between the connection member 40 and the ring member 34 using the adhesive may be performed not only between the arm sections 40c and the engaging pawls 34b but also between the rear end face of the ring member 34 and the pawl sections 40d of the connection member 40.

Hence, in this embodiment, the mounting frame section 40a of the connection member 40 is fastened to the end section 39a of the cable cover 39, and the pawl sections 40d of the connection member 40 are engaged with the prism mounting frame 33b of the prism holder 33. Furthermore, the pawl sections 40d of the connection member 40 are held between the prism mounting frame 33b and the ring member 34. Hence, even if an external force is applied to the signal cable 37 and the pawl sections 40d of the connection member 40 are pulled in a direction away from the engaged position, for example, when the insertion section 11 of the endoscope 10 is bent, the engagement at the pawl sections 40d can be maintained against this tension force. As a result, the connection strength of the connection member 40 against the tension force applied to the signal cable 37 can be improved.

In addition, since the ring member 34 is screw-fastened to the interior of the tip hard section 14 of the endoscope 10 while holding the pawl sections 40d of the connection member 40 between the ring member 34 and the prism mounting frame 33b of the prism holder 33, the force for holding the pawl sections 40d therebetween can be maintained.

Furthermore, in the case that the ring member 34 has the pair of engaging pawls 34b shown in FIG. 5, the engaging pawls 34b stride the rear end face of the prism mounting frame 33b and are engaged with the arm sections 40c of the connection member 40 from the outside. Since the engaging pawls 34b hold the sides of the prism mounting frame 33b therebetween via the arm sections 40c of the connection member 40, the engagement between the connection member 40 and the prism holder 33 can be maintained against the stress applied in this holding direction. Moreover, since the ring member 34 is fastened to the connection member 40 using the adhesive, the connection strength between the connection member 40 and the prism holder 33 using the ring member 34 for holding the pawl sections 40d of the connection member 40 can be improved further.

Still further, since the engaging pawls 34b stride the rear end face of the prism mounting frame 33b to which the prism 27 is bonded, the prism mounting frame 33b can be protected from the stress applied in the direction of holding the prism mounting frame 33b between the engaging pawls 34b. As a result, it is possible to prevent a situation in which the prism mounting frame 33b is deflected by the stress and the prism 27 is separated.

As described above, the endoscope disclosed in this specification is equipped with a solid-state imaging device for photoelectrically converting optical images formed via an imaging lens; a circuit board electrically connected to the solid-state imaging device; a signal cable electrically connected to the circuit board; an optical member holding section for holding the imaging lens or a prism; a connection member, one end of which is fastened to the signal cable and the other end of which is provided with engaging pawls to be engaged with the optical member holding section, for connecting the optical member holding section to the signal cable; and a mounting member to be mounted on at least part of the outer periphery of the optical member holding section, wherein the mounting member makes contact with the engaging pawls engaged with the optical member holding section to hold at least part of the engaging pawls between the mounting member and the optical member holding section.

Furthermore, the mounting member is fastened to the body section of the endoscope.

Moreover, the optical member holding section holds the prism on the end face thereof, and the mounting member has engaging pawls that stride the end face on which the prism is held and are engaged with the connection member.

Although the invention has been described above in relation to preferred embodiments and modifications thereof, it will be understood by those skilled in the art that other variations and modifications can be effected in these preferred embodiments without departing from the scope and spirit of the invention.

What is claimed is:

1. An endoscope comprising:
   a solid-state imaging device for photoelectrically converting optical images formed via an imaging lens,
   a circuit board electrically connected to the solid-state imaging device,
   a signal cable electrically connected to the circuit board,
   an optical member holding section that holds the imaging lens or a prism,
   a connection member, one end of which is fastened to the signal cable and other end of which is provided with engaging pawls to be engaged with the optical member holding section, that connects the optical member holding section to the signal cable, and a mounting member that is mounted on at least part of an outer periphery of the optical member holding section, wherein the mounting member makes contact with the engaging pawls engaged with the optical member holding section to hold at least part of the engaging pawls between the mounting member and the optical member holding section.

2. The endoscope according to claim 1, wherein the mounting member is fastened to a body section of the endoscope.

3. The endoscope according to claim 1, wherein the optical member holding section holds the prism on an end face of the optical member holding section, and the mounting member has engaging pawls that stride the end face on which the prism is held and are engaged with the connection member.

4. The endoscope according to claim 2, wherein the optical member holding section holds the prism on an end face of the optical member holding section, and the mounting member has engaging pawls that stride the end face on which the prism is held and are engaged with the connection member.

* * * * *